United States Patent
Seo et al.

(12) 
(10) Patent No.: US 12,320,747 B2
(45) Date of Patent: *Jun. 3, 2025

(54) APPARATUS AND METHOD FOR PCR DIAGNOSIS BASED ON MULTI-WAVELENGTH LIGHT SOURCE AND ORTHOGONAL CODE SIGNALS

(71) Applicant: ELECTRONICS AND TELECOMMUNICATIONS RESEARCH INSTITUTE, Daejeon (KR)

(72) Inventors: Hong-Seok Seo, Daejeon (KR); Dong Hoon Song, Daejeon (KR); Jeong Won Park, Daejeon (KR); Chul Huh, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 239 days.

This patent is subject to a terminal disclaimer.

(21) Appl. No.: 17/884,667

(22) Filed: Aug. 10, 2022

(65) Prior Publication Data
US 2023/0141045 A1 May 11, 2023

(30) Foreign Application Priority Data

Nov. 8, 2021 (KR) .................. 10-2021-0152485
Apr. 19, 2022 (KR) .................. 10-2022-0048415

(51) Int. Cl.
*G01N 21/552* (2014.01)
*C12Q 1/686* (2018.01)

(52) U.S. Cl.
CPC .......... *G01N 21/554* (2013.01); *C12Q 1/686* (2013.01)

(58) Field of Classification Search
CPC  C12Q 1/686; C12Q 2563/107; C12Q 1/6818; C12Q 2537/165; G01N 21/6428;
(Continued)

(56) References Cited

U.S. PATENT DOCUMENTS 6,144,448 A  11/2000  Mitoma
8,137,616 B2  3/2012  Sagner et al.
(Continued)

FOREIGN PATENT DOCUMENTS

DE  112016002209 T5 *  3/2018  ............. G01N 21/01
JP  H06-034546 A  2/1994
(Continued)

OTHER PUBLICATIONS

Cosimo D'Andrea et al., "The study of polyplex formation and stability by time-resolved fluorescence spectroscopy of SYBR Green I-stained DNA", Photochem. Photobiol. Sci., 2014, 13, 1680-1689.
(Continued)

*Primary Examiner* — Sunghee Y Gray
(74) *Attorney, Agent, or Firm* — LRK PATENT LAW FIRM

(57) ABSTRACT

Disclosed is a PCR diagnosis apparatus, which includes a transmitter including a multi-wavelength light source for outputting a first light source signal and a second light source signal having different wavelengths, and that applies the first light source signal and the second light source signal to a PCR chip including samples each including a plurality of DNAs, a code generator that generates first code signal and second code signal corresponding to the first light source signal and the second light source signal, respectively, and which are orthogonal to each other, and a receiver that performs a dot product on fluorescent data and each of the first code signal and the second code signal, wherein the fluorescent data include a first fluorescent signal and a
(Continued)

second fluorescent signal emitted from a phosphor attached to each of the plurality of DNAs.

9 Claims, 7 Drawing Sheets

(58) Field of Classification Search
CPC ............. G01N 21/645; G01N 21/6486; G01N 27/4167; G01N 2021/6419; G01N 21/554; B01L 2200/0663; C08F 2500/17; C08K 2003/2206; C08K 2003/222; C08K 2003/2227; C08K 2003/2296; C08K 2003/328; C08K 3/22; C08K 5/17; C08L 2203/02; C08L 83/04
USPC ........................................................ 356/445
See application file for complete search history.

(56) References Cited

U.S. PATENT DOCUMENTS

| | | |
|---|---|---|
| 10,138,513 B2 | 11/2018 | Chung et al. |
| 10,345,243 B2 | 7/2019 | Lee et al. |
| 11,920,191 B2 | 3/2024 | Chen et al. |
| 2004/0120455 A1* | 6/2004 | Luryi .................. G01N 21/645 378/44 |
| 2008/0253409 A1 | 10/2008 | Moon |
| 2008/0283754 A1 | 11/2008 | Nerin et al. |
| 2018/0080064 A1* | 3/2018 | Lee .......................... B01L 7/52 |
| 2018/0156755 A1 | 6/2018 | Jeong et al. |

FOREIGN PATENT DOCUMENTS

| | | |
|---|---|---|
| KR | 10-2008-0007473 A | 1/2008 |
| KR | 10-0818351 B1 | 4/2008 |
| KR | 10-2017-0125838 A | 11/2017 |
| KR | 10-2018-0123867 A | 11/2018 |
| WO | 2011/077203 A2 | 6/2011 |

OTHER PUBLICATIONS

E.S. Fotso Guetue et al., "Nanosecond time resolved Raman spectroscopy for solving some Raman problems such as luminescence or thermal emission", Journal of Raman Spectroscopy, 2018.

* cited by examiner

FIG. 2A

CODE1: 1, 0, 0, 1, 0, 1, 1, 0, 0, 1, 1, 0, 1, 0, 0, 1

CODE2: 0, 1, 1, 0, 1, 0, 0, 1, 0, 1, 1, 0, 1, 0, 0, 1

CODE3: 0, 1, 0, 1, 0, 1, 0, 1, 0, 1, 0, 1, 0, 1, 0, 1

CODE4: 0, 0, 1, 1, 0, 0, 1, 1, 0, 0, 1, 1, 0, 0, 1, 1

CODE5: 1, 1, 0, 0, 1, 1, 0, 0, 0, 0, 1, 1, 0, 0, 1, 1

CODE6: 1, 0, 1, 0, 0, 1, 0, 1, 1, 0, 1, 0, 0, 1, 0, 1

APPARATUS AND METHOD FOR PCR DIAGNOSIS BASED ON MULTI-WAVELENGTH LIGHT SOURCE AND ORTHOGONAL CODE SIGNALS

CROSS-REFERENCE TO RELATED APPLICATIONS

This application claims priority under 35 U.S.C. § 119 to Korean Patent Application No. 10-2021-0152485, filed on Nov. 8, 2021, and Korean Patent Application No. 10-2022-0048415, filed on Apr. 19, 2022, in the Korean Intellectual Property Office, the disclosures of which are incorporated by reference herein in their entireties.

BACKGROUND

1. Field of the Invention

Embodiments of the present disclosure described herein relate to a diagnosis apparatus, and more particularly, relate to an apparatus and a method for a PCR diagnosis based on a multi-wavelength light source and orthogonal code signals.

2. Description of Related Art

Molecular diagnosis technology is a technology that analyzes molecules that cause diseases in a body, such as diseases caused by viruses and other genetic diseases. Using molecular diagnosis technology, whether a molecule contains disease-causing DNAs may be analyzed with great precision through a DNA amplification. Molecular diagnosis technology involves a process of extracting DNAs by pre-processing a bio sample to be measured, and a process of replicating and amplifying the desired part of the extracted DNAs using a polymerase chain reaction (PCR). After attaching a phosphor (e.g., a SYBR green) to the amplified DNAs, an intensity of the fluorescent signal emitted by an optical method may be measured. When there is emission of fluorescent corresponding to the attached phosphor, it is determined that the sample contains DNAs causing diseases.

As the DNA is amplified more, more phosphors may be attached and the intensity of fluorescent may increase. In the case of general PCR, the amplification process involves 30 cycle counts, and 230 DNA chains are replicated. Using conventional PCR, it takes about 4 hours to prepare bio samples and to proceed with 30 cycles of amplification. In addition, it is possible to detect multiple DNAs at once in one sample. To this end, it is common to configure two or more phosphors and use a multi-wavelength light source. The multi-wavelength light source used in conventional PCR is continuous light (white light).

However, when continuous light is used to detect a plurality of DNAs at once, there is an issue in that noise is generated since signals generated from phosphors not attached to DNA chains are mixed as well as signals generated from multiple phosphors. In addition, there is an issue (i.e., a photo bleaching) in which the fluorescent intensity with respect to continuous light of the phosphor decreases over time. Therefore, there is a need for a technology capable of accurately and efficiently detecting a signal generated from a phosphor while minimizing the PCR amplification cycle count.

SUMMARY

Embodiments of the present disclosure provide an apparatus and method for a PCR diagnosis capable of minimizing a DNA amplification cycle count to analyze a plurality of DNAs simultaneously and improving detection accuracy.

According to an embodiment of the present disclosure, a PCR diagnosis apparatus includes a transmitter including a multi-wavelength light source for outputting a first light source signal and a second light source signal having different wavelengths, and that applies the first light source signal and the second light source signal to a PCR chip including samples each including a plurality of DNAs, a code generator that generates first code signal and second code signal corresponding to the first light source signal and the second light source signal, respectively, and which are orthogonal to each other, and a receiver that performs a dot product on fluorescent data and each of the first code signal and the second code signal, wherein the fluorescent data include a first fluorescent signal and a second fluorescent signal emitted from a phosphor attached to each of the plurality of DNAs, and the first fluorescent signal is emitted from a first phosphor attached to a first DNA among the plurality of DNAs in response to the first light source signal, and the second fluorescent signal is emitted from a second phosphor attached to a second DNA among the plurality of DNAs in response to the second light source signal.

According to an embodiment of the present disclosure, a PCR diagnosis method includes generating a plurality of code signals orthogonal to each other, modulating a plurality of light source signals having different wavelengths based on the plurality of code signals and applying the modulated light source signals to a PCR chip including samples each including a plurality of DNAs, and performing a dot product on fluorescent data including a plurality of fluorescent signals emitted from a phosphor attached to each of the plurality of DNAs and each of the plurality of code signals.

BRIEF DESCRIPTION OF THE FIGURES

The above and other objects and features of the present disclosure will become apparent by describing in detail embodiments thereof with reference to the accompanying drawings.

FIG. 2A is a diagram illustrating an example of a code signal generated by a code generator of FIG. 1.

DETAILED DESCRIPTION

Hereinafter, embodiments of the present disclosure will be described clearly and in detail such that those skilled in the art may easily carry out the present disclosure.

Components that are described in the detailed description with reference to the terms "unit", "module", "block", "~er or ~or", etc. and function blocks illustrated in drawings will be implemented with software, hardware, or a combination thereof. For example, the software may be a machine code, firmware, an embedded code, and application software. For example, the hardware may include an electrical circuit, an electronic circuit, a processor, a computer, an integrated circuit, integrated circuit cores, a pressure sensor, an inertial sensor, a microelectromechanical system (MEMS), a passive element, or a combination thereof.

Figure 1:
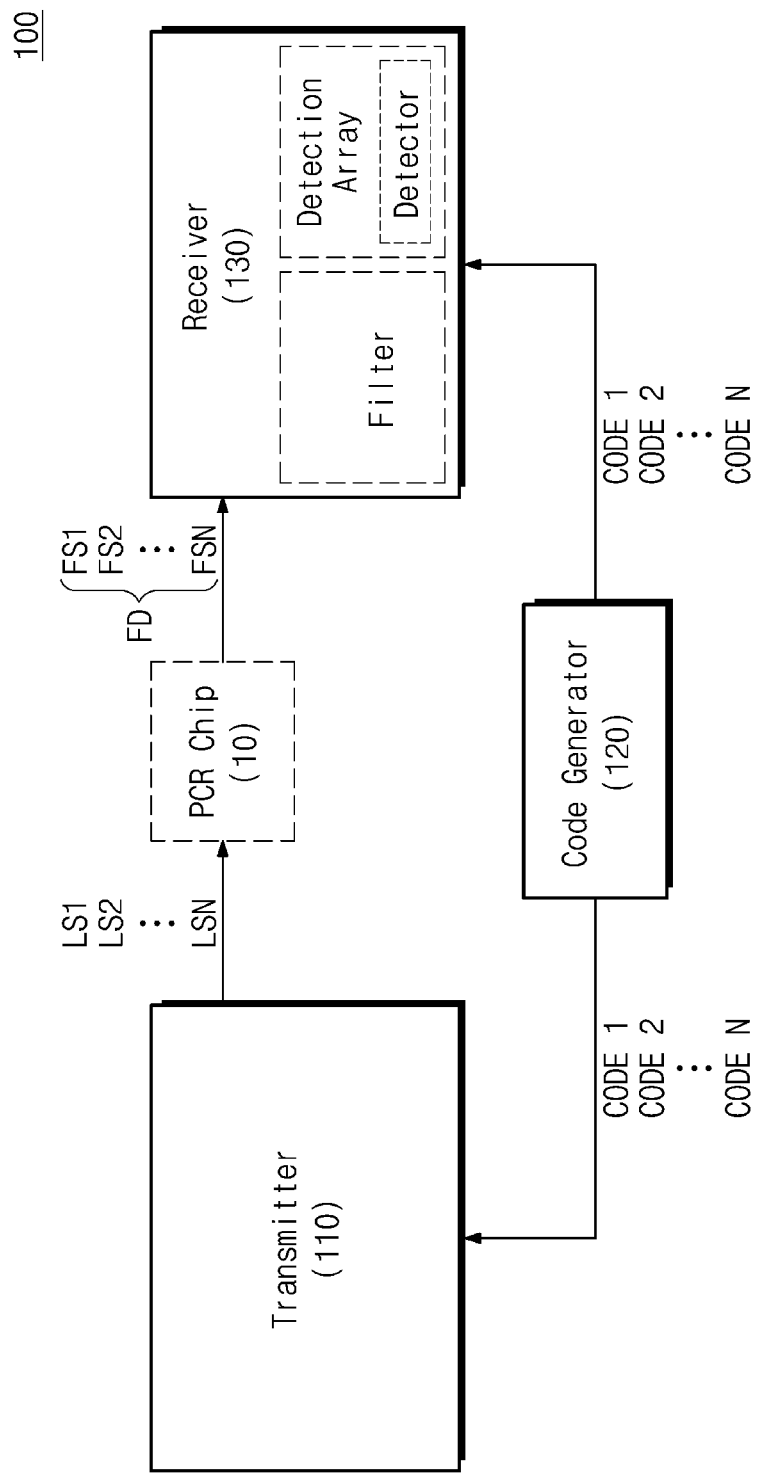
FIG. 1 is a diagram illustrating an apparatus for a PCR diagnosis, according to an embodiment of the present disclosure.

FIG. 1 illustrates an apparatus 100 for a PCR diagnosis, according to an embodiment of the present disclosure. The apparatus 100 may apply a plurality of light source signals LS1 to LSN to a PCR chip 10 including samples including a plurality of DNAs to which phosphors are attached. The phosphor attached to each DNA in the samples of the PCR chip 10 may emit fluorescent signals FS1 to FSN in response to the received light source signals LS1 to LSN. The apparatus 100 may receive the fluorescent signals FS1 to FSN emitted from the samples of the PCR chip 10, and may detect the plurality of DNAs to be analyzed. The apparatus 100 may include a transmitter 110, a code generator 120, and a receiver 130.

The transmitter 110 may include a plurality of multi-wavelength light sources to be applied to the samples of the PCR chip 10. For example, each of the plurality of light sources may be any one of a laser diode (LD) or a light emitting diode (LED) having a limited wavelength. Hereinafter, it is assumed that the plurality of light sources of the present disclosure are LDs for clarity, but the present disclosure is not limited thereto. In addition, hereinafter, it is assumed that the light source of the present disclosure is a multi-wavelength light source. The number of the plurality of light sources may be the same as the number of different phosphors attached to the plurality of DNAs in the samples of the PCR chip 10.

The plurality of light source signals LS1 to LSN may be signals in which signals output from the plurality of light sources are modulated based on one of a plurality of code signals CODE1 to CODEN received from the code generator 120. The transmitter 110 may include at least one of a circuit, software, and firmware for modulating signals output from the plurality of light sources based on one of the plurality of code signals CODE1 to CODEN.

For example, a level of the signal output from the plurality of light sources may be modulated to be equal to the original level while a level of the code signal maintains a logic high value, and to be '0' while the level of the code signal maintains a logic low value. For example, the signals output from the plurality of light sources may be modulated by a pulse amplitude modulation (PAM) method based on one of the plurality of code signals CODE1 to CODEN.

The transmitter 110 may include a plurality of optical fiber bundles for applying the modulated light source signals LS1 to LSN to the samples of the PCR chip 10. Each light source signal LS1 to LSN having a different wavelength may be transmitted through a corresponding optical fiber bundle, and may be combined in one output optical fiber through an optical fiber combiner that uses a wavelength division multiplexing (WDM) or a space division multiplexing. The output optical fiber may include a collimator or a splitter at an end thereof, and each of the light source signal LS1 to LSN having different wavelengths may be applied to the plurality of DNAs.

The code generator 120 may generate the plurality of code signals CODE1 to CODEN for modulating signals output from a plurality of light sources of the transmitter 110. For example, each of the plurality of code signals CODE1 to CODEN may be a pulse signal having a logic high value or a logic low value. In particular, the plurality of code signals CODE1 to CODEN generated by the code generator 120 of the present disclosure may be orthogonal to each other. The code generator 120 may modulate signals output from the light sources by applying one of the plurality of code signals CODE1 to CODEN orthogonal to each other to each light source having a different wavelength.

Specifically, a level of the modulated light source signals LS1 to LSN may be the same as a level of a signal originally output from the light source while a level of the corresponding code signal is maintained at a logic high value, and may be the level of '0' where the light source is turned off while the level of the corresponding code signal is maintained at a logic low value. In detail, each of the modulated light source signals LS1 to LSN may be applied to the samples of the PCR chip 10 while the level of the corresponding code signal is maintained at a logic high value.

For example, the time at which the signal level starts to rise from the logic low value to the logic high value and the time at which the signal level starts to fall from the logic high value to the logic low value may be different for each of the code signals CODE1 to CODEN applied to each light source having a different wavelength. As a result, each of the light source signals LS1 to LSN having different wavelengths may be temporally dispersed and applied to the samples of the PCR chip 10. Furthermore, the code generator 120 may transmit the generated code signals CODE1 to CODEN to the receiver 130. The code signals CODE1 to CODEN that are orthogonal to each other of the present disclosure will be described in more detail with reference to FIG. 2.

Different phosphors may be attached to each of the plurality of DNAs in the samples inside the PCR chip 10. The different phosphors may absorb the light source signals LS1 to LSN having different wavelengths. The phosphor attached to each DNA may emit a fluorescent signal by absorbing a relevant light source signal. For example, the phosphor may be a SYBR green phosphor that absorbs a light source having a wavelength of 530 nm or less and emits a fluorescent signal having a wavelength of 550 nm or more.

Accordingly, the phosphor attached to each DNA of the present disclosure may absorb the light source signals LS1 to LSN having different wavelengths at different times determined based on the code signals CODE1 to CODEN, and may emit the fluorescent signals FS1 to FSN corresponding to wavelengths of absorbed light source signals LS. The fluorescent signals FS1 to FSN emitted from each phosphor may be provided to the receiver 130.

The receiver 130 may receive fluorescent data FD, and the fluorescent data may include the fluorescent signals FS1 to FSN emitted from phosphors attached to each DNA in samples inside the PCR chip 10. The receiver 130 may include the plurality of optical fiber bundles to receive the fluorescent data FD. Since some of the light source signals LS1 to LSN are reflected from samples inside the PCR chip 10 and transmitted through the plurality of optical fiber bundles, a filter for removing the light source signals LS1 to LSN may be located at the ends of the plurality of optical fiber bundles. In addition, a detection array (e.g., a silicon detection array) for converting the fluorescent data FD into an electrical signal may be located at the ends of the plurality of optical fiber bundles. The detection array may include a plurality of detectors that receive the fluorescent data FD.

Accordingly, the receiver 130 may receive only the fluorescent data FD from the samples inside the PCR chip 10 by removing the light source signals LS1 to LSN reflected from the samples inside the PCR chip 10 and transmitted through the optical fiber bundles using the filter. In addition, the fluorescent data FD derived from the samples inside the PCR chip 10 may be converted into an electrical signal through the detection array.

Furthermore, the receiver 130 may receive the plurality of code signals CODE1 to CODEN that are orthogonal to each other from the code generator 120. In particular, the plurality of detectors of the receiver 130 may perform a dot product on the fluorescent data FD and the plurality of code signals CODE1 to CODEN, and may receive the performed result as a measurement signal. The receiver 130 may include at least one of a circuit, software, and firmware for performing a dot product on the fluorescent data FD and the code signals CODE1 to CODEN. A specific embodiment of performing the dot product on the fluorescent data FD and the code signals CODE1 to CODEN will be described in detail with reference to FIGS. 2A to 2B below.

Among the fluorescent signals FS1 to FSN included in the input fluorescent data FD, a fluorescent signal of which coding matches the code signal will not be orthogonal to the code signal, so may be accumulated when the dot product for the fluorescent data FD and the code signal is performed (i.e., a higher signal intensity than the original fluorescent signal may be obtained). In contrast, the fluorescent signals of which coding does not match the code signals will be orthogonal to the code signals, so may be accumulated even when the dot product on the fluorescent data FD and the code signal is performed. Accordingly, the fluorescent signal matching the received code signal is summed by performing the dot product to obtain a higher signal strength, thereby increasing a gain and minimizing the number of the DNA replication cycles of the PCR system.

FIG. 2A illustrates an example of a code signal generated by the code generator 120 of FIG. 1. As described with reference to FIG. 1, the code signals CODE1 to CODEN of the present disclosure may be a pulse signal having a logic high value (indicated by "1" in FIG. 2) or a logic low value (indicated by "0" in FIG. 2). In addition, the code signals CODE1 to CODEN of the present disclosure are orthogonal to each other. Hereinafter, it will be described with reference to FIG. 1 together with FIG. 2A.

For clarity, it is assumed that the transmitter 110 includes six light sources LD1 to LD6 having different wavelengths, and the six light sources LD1 to LD6 output first to sixth light source signals LS1 to LS6, respectively. Also, it is assumed that the code generator 120 generates six code signals CODE1 to CODE6 that respectively correspond to the six light source signals LS1 to LS6 and are orthogonal to one another. Also, it is assumed that the length of each of the code signals CODE1 to CODE6 is 16 bits. However, the present disclosure is not limited thereto, and the number of light sources, the number of code signals, or the length of the code signals may vary.

The time for which the level of each code signal CODE1 to CODE6 is maintained at a logic high value (i.e., the duration of '1') and the time for which the level of each code signal CODE1 to CODE6 is maintained at a logic low value (that is, the duration of '0') may be changed according to the performance of the receiver 130. In addition, as the total number of bits of the code signal increases, a gain may increase.

In each of the code signals CODE1 to CODE6 orthogonal to each other, the number of '1' (i.e., the total time that the level is maintained at a logic high value) and the number of '0' (i.e., the total time that the level is maintained at a logic low value) are equal to each other. In the case of code signals orthogonal to each other, after '−1' is substituted in the digit of '1' of each code signal CODE1 to CODE6 and '1' is substituted in the digit of '0' of each code signal CODE1 to CODE6, the result obtained by performing the dot product between the code signals becomes '0'.

For example, when '−1' and '1' are substituted into '1' and '0' digits of the first code signal CODE1 and the second code signal CODE2, respectively, as follows.

CODE1: −1, 1, 1, −1, 1, −1, −1, 1, 1, −1, −1, 1, −1, 1, 1, −1

CODE2: 1, −1, −1, 1, −1, 1, 1, −1, 1, −1, −1, 1, −1, 1, 1, −1

When the dot product is performed, it is calculated as $(-1)*1+1*(-1)+1*(-1)+(-1)*1+1*(-1)+(-1)*1+(-1)*1+1*(-1)+1*1+(-1)*(-1)+(-1)*(-1)+1*1+(-1)*(-1)+1*1+1*1+(-1)*(-1)$, and the result becomes '0'. In contrast, even when '1' is substituted into '1' digit and '−1' is substituted into '0' digit, the result is '0', which is the same as in the above case. When the dot product is performed with respect to any two code signals among the remaining code signals in the same way as described above, the result is '0'. That is, it may be confirmed that each of the code signals CODE1 to CODE6 of FIG. 2 are orthogonal to one another.

As described with reference to FIG. 1, the code signals CODE1 to CODE6 orthogonal to each other may be applied to the transmitter 110 to modulate the light source signals having different wavelengths. In detail, the light source signals having different wavelengths may be coded to be orthogonal to each other, and fluorescent signals emitted by each DNA in each sample of the PCR chip 10 in response to the light source signal may also be orthogonal to each other. Accordingly, the fluorescent signals and the code signals may also be orthogonal to each other.

For example, the dot product result on the fluorescent signal generated based on the light source signal to which the first code signal CODE1 is applied and the second code signal CODE2 may become '0'. However, since the phosphor actually attached to the DNA receives not only the light source signals but also the noise or interference signal, the dot product on the fluorescent signal and the code signal orthogonal to each other may have a value close to '0' instead of '0'.

For example, the level of the fluorescent signal corresponding to a section in which the level of the code signal is logic high (i.e., a section in which the value of the code signal is '1') may be a value dependent on the number of PCR cycles, and the level of the fluorescent signal corresponding to a section in which the level of the code signal is logic low (i.e., a section in which the value of the code signal is '0') may be noise or an interference signal caused by another adjacent light source. For example, the value dependent on the number of PCR cycles may be a value greater than a magnitude of the noise or interference signal.

Specifically, it is assumed that the six code signals CODE1 to CODE6 modulate the six light source signals LS1 to LS6 having different wavelengths, and the six light source signals LS1 to LS6 are simultaneously applied to each sample of the PCR chip 10, simultaneously for the PCR. In this case, it is assumed that the PCR chip 10 includes 'n' samples, and it is assumed that each sample contains different DNAs to which 6 phosphors are attached. The fluorescent data including six fluorescent signals emitted from a first sample may be provided to a first detector of the receiver 130, and the fluorescent data including six fluorescent signals emitted from a second sample may be provided to a second detector of the receiver 130. As in the above description, the fluorescent data including six fluorescent signals emitted from an n-th sample may be provided to an n-th detector of the receiver 130. Since it is previously assumed that the length of each of the code signal CODE1 to CODE6 is 16 bits, the length of the fluorescent data received to each detector is also 16 bits. For example, the value of fluorescent data DS1 received by the first detector may be represented as $a_1, a_2, \ldots a_{16}$.

Figure 2B:
FIG. 2B is a table illustrating an example of a fluorescent signal received by a first detector among a plurality of detectors of a receiver, and explains how to perform a dot product between a fluorescent data received by a first detector and a code signal 1.

FIG. 2B illustrates an example of the fluorescent data DS1 received to the first detector among the plurality of detectors of the receiver 130. As described with reference to FIG. 1, the fluorescent data may include a plurality of fluorescent signals. For example, the fluorescent data DS1 received to the first detector may be a signal obtained by adding six fluorescent signals FS1 to FS6 emitted from the first sample.

For example, when the dot product is performed with respect to the fluorescent data DS1 and the first code CODE1, an accumulative sum of the first fluorescent signal FS1 emitted by the first light source signal LS1 may be obtained. As in the above description, when the dot product is performed with respect to the fluorescent data DS1 and the sixth code CODE6, an accumulative sum of the sixth fluorescent signal FS6 emitted by the sixth light source signal LS6 may be obtained. The accumulative sum of other fluorescent signals may be calculated in the same way.

For example, the dot product on the fluorescent data DS1 and the first code CODE1 may be performed by converting the first code CODE1 by substituting '−1' into the digit of '0' and substituting '1' into the digit of '1' of the first code CODE1, and then by calculating a dot product on the converted first code CODE1 and the fluorescent data DS1. As described above, the dot product result is the accumulative sum of the first fluorescence signals FS1 emitted from the first sample after the first light source signal LS1 is applied to the first sample. In detail, the accumulative sum may correspond to a signal obtained by adding the first fluorescent signal FS1 received to the first detector based on the logic that the first light source signal LS1 is generated in the first light source LD1.

Referring to FIG. 2B, the calculated dot product result (CODE1·DS1; the accumulative sum of the first fluorescent signal FS1 received to the first detector) is $1*a_1+(-1)*a_2+(-1)*a_3+1*a_4+(-1)*a_5+1*a_6+1*a_7+(-1)*a_8+(-1)*a_9+1*a_{10}+1*a_{11}+(-1)*a_{12}+1*a_{13}+(-1)*a_{14}+(-1)*a_{15}+1*a_{16}$.

In this case, the accumulative sum of the first fluorescent signals FS1 may be a value accumulated by the number of '1' included in the corresponding first code signal CODE1 compared to the first fluorescent signal FS1. That is, in the above-described example, since the number of '1' included in the first code signal CODE1 is '8', the accumulative sum of the first fluorescent signals FS1 may have a gain of 8 times compared to the gain of the first fluorescent signal FS1. Since the first fluorescent signal FS1 generated by the first light source signal LS1 is orthogonal to fluorescent signals (e.g., FS2 to FS6) with different wavelengths, the first fluorescent signal FS1 does not affect the accumulative sum of other fluorescent signals.

As in the above description, the accumulated sum of each of the second to sixth fluorescent signals FS2 to FS6 generated by applying the second to sixth light source signals LS2 to LS6 to the first sample may be calculated by performing the dot product on the fluorescence data DS1 received to the first detector DS1 and the second to sixth code signals CODE2 to CODE6, respectively. The accumulative sum of fluorescent signals formed by different DNAs in different samples of the PCR chip 10 may also be calculated in the same way.

As described above, the fluorescent signal emitted from each DNA included in each sample of the PCR chip 10 may be separated by performing the dot product on the corresponding code signal and the fluorescent data received to the detector. In addition, since a plurality of light source signals are simultaneously applied to each sample, the above-described process may be processed in parallel, and the PCR may be performed quickly.

However, the present disclosure is not limited to that described above with reference to FIGS. 2A to 2B, and the code signals generated by the code generator 120 may be pulse signals in which logic high ("1") and logic low ("0") values appear alternately and are orthogonal to each other, unlike the first to sixth code signals CODE1 to CODE6 illustrated in FIG. 2. Also, the dot product on the fluorescent data and the code signal may be performed in a method other than the above.

Figure 3:
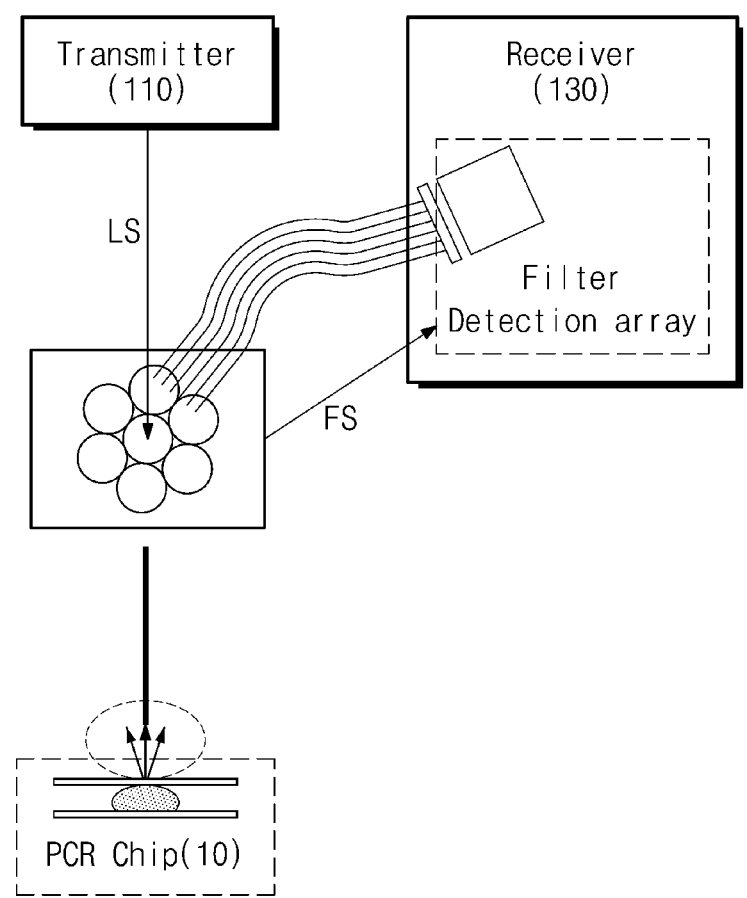
FIG. 3 is a diagram illustrating a structure of an optical fiber included in an apparatus of FIG. 1.

FIG. 3 illustrates a structure of an optical fiber included in the device 100 of FIG. 1. The light source signal LS output from the light source of the transmitter 110 may be simultaneously applied to each sample of the PCR chip 10 through a central optical fiber of the optical fiber bundle. The fluorescent signal FS emitted from the phosphors attached to the DNA of the sample of the PCR chip 10 in response to the light source signal LS may be provided to the detection array of the receiver 130 through outer optical fibers of the optical fiber bundle, the fluorescent signal FS in the detection array may be converted into an electrical signal. In addition, some of the light source signal LS reflected from the samples may be removed by the filter. Therefore, according to an embodiment of the present disclosure, a fluorescent signal FS of weak intensity emitted from a phosphor attached to the DNA may be transmitted through a plurality of optical fiber bundles, thereby minimizing the loss of the fluorescent signal FS.

Figure 4:
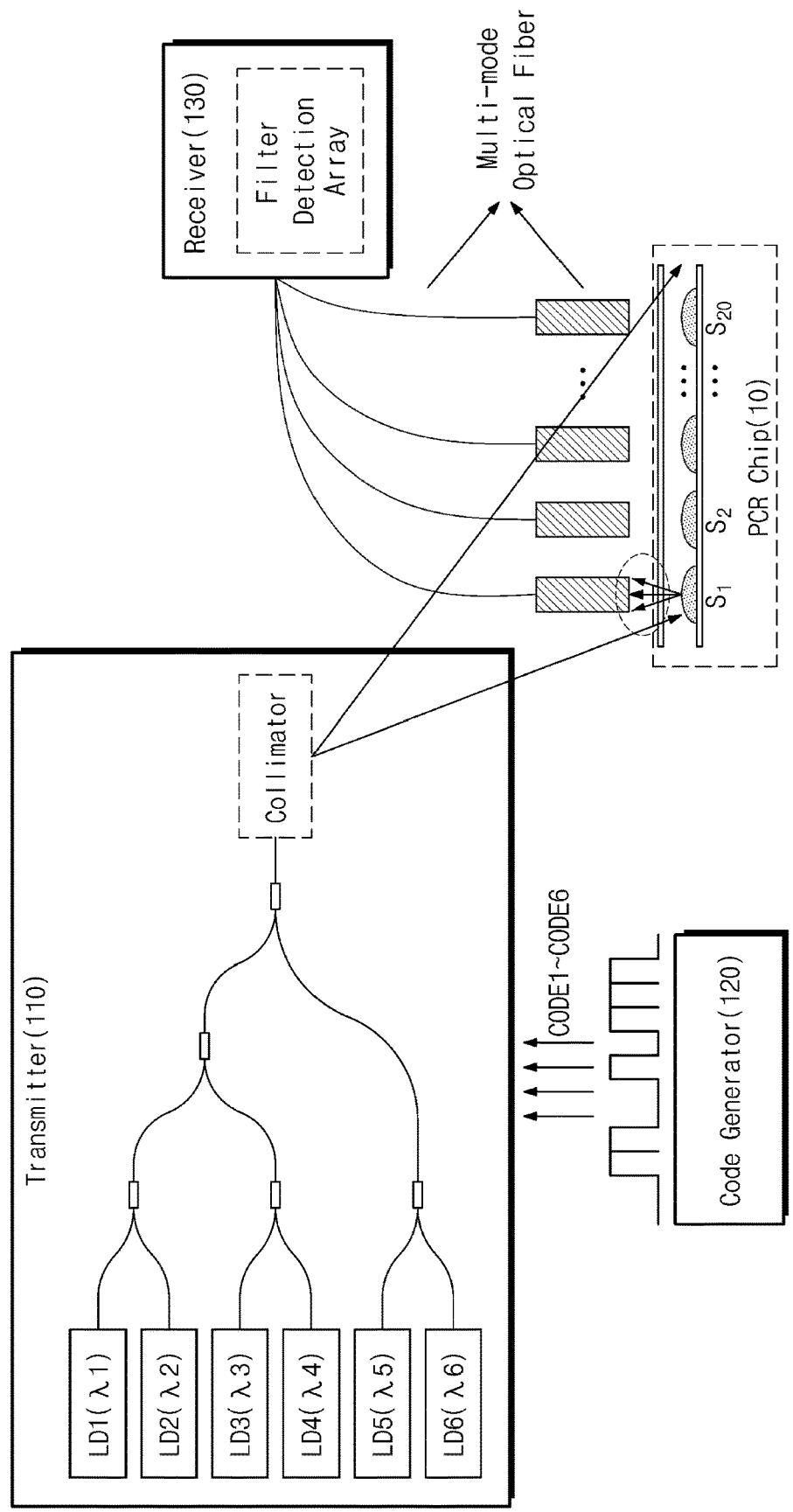
FIG. 4 is a diagram conceptually illustrating an operation of an apparatus for a PCR diagnosis, according to an embodiment of the present disclosure.

FIG. 4 conceptually illustrating an operation of the apparatus 100 for a PCR diagnosis, according to an embodiment of the present disclosure.

The PCR chip 10 illustrated in FIG. 4 may include samples s1 to s20 containing a plurality of DNA, and phosphors may be attached to each DNA of each of the samples s1 to s20. The phosphor attached to the DNA of each of the samples s1 to s20 may absorb a light source signal having a corresponding wavelength to emit a fluorescent signal.

It is assumed that the number of different phosphors attached to the DNA of each of the samples s1 to s20 in FIG. 4 is six, and the transmitter 110 includes the first to sixth light sources LD1 to LD6 respectively corresponding to the six different phosphors. The first to sixth light sources LD1 to LD6 may have different first to sixth wavelengths λ1 to λ6, respectively. However, the present disclosure is not limited thereto, and the number of samples, the number of phosphors, and the number of light sources included in the PCR chip 10 may be set differently from those illustrated in FIG. 4.

The first to sixth light sources LD1 to LD6 are respectively connected to an optical fiber bundle, and the first to sixth light source signals LS1 to LS6 may be output through the corresponding optical fiber bundle. The first to sixth light source signals LS1 to LS6 may be output from the code generator 120 and may be modulated by the first to sixth code signals CODE1 to CODE6 that are orthogonal to each other, as described with reference to FIGS. 1 to 2.

As described with reference to FIG. 1, the first to sixth light source signals LS1 to LS6 may be combined in one output optical fiber through an optical fiber combiner that performs a combine operation using a wavelength division multiplexing (WDM) or a space division multiplexing. The output optical fiber may include a collimator at an end thereof, and the first to sixth light source signals LS1 to LS6 having different wavelengths λ1 to λ6 may be applied simultaneously to the plurality of samples s1 to s20 through the collimator.

The phosphor attached to the plurality of DNAs in the plurality of samples s1 to s20 may absorb the first to sixth light source signals LS1 to LS6 at different times according to codes through the plurality of optical fiber bundles. Accordingly, the first to sixth fluorescent signals FS1 to FS6 may be emitted for each sample. The first to sixth fluorescent signals FS1 to FS6 emitted from each of the samples s1 to s20 of the PCR chip 10 may be converted into an electrical signal in a detection array of the receiver 130 through the plurality of optical fiber bundles. In addition, the code generator 120 may transmit the first to sixth code signals CODE1 to CODE6 to the receiver 130. Each of the detectors included in the detection array of the receiver 130 may perform a dot product on the first to sixth fluorescent signals FS1 to FS6 and the first to sixth code signals CODE1 to CODE6. Accordingly, the apparatus 100 may detect an expression level of each DNA in the plurality of samples s1 to s20 based on a dot product fluorescent value.

On the other hand, as described with reference to FIG. 1, since some of the first to sixth light source signals LS1 to LS6 are reflected from the sample of the PCR chip 10 and may transmitted through the plurality of optical fiber bundles, a filter for removing the light source signal may be located at the ends of the plurality of optical fiber bundles. For example, since an orthogonal code of the first fluorescent signal FS1 generated based on the first light source signal LS1 is the same as an orthogonal code of the first light source signal LS1, the receiver 130 cannot distinguish the light source signal from the fluorescent signal based on only the orthogonal code. Therefore, the light source signal used for generating the fluorescent signal should be removed by the filter such that the light source signal does not enter the detection array.

Figure 5:
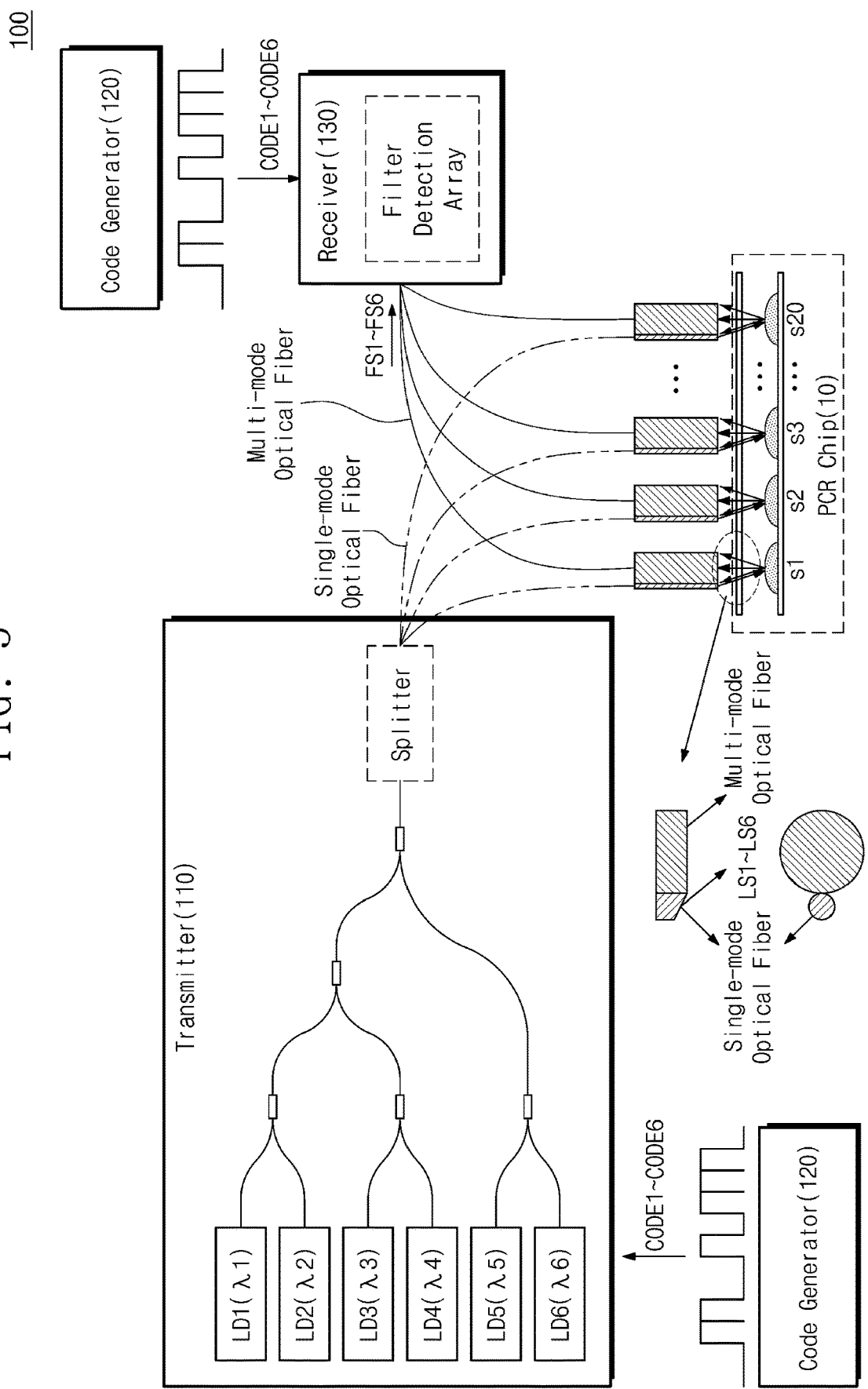
FIG. 5 is a diagram conceptually illustrating an operation of an apparatus for a PCR diagnosis, according to another embodiment of the present disclosure.

FIG. 5 conceptually illustrates an operation of the apparatus 100 for a PCR diagnosis, according to another embodiment of the present disclosure.

Unlike the case where, in FIG. 4, the first to sixth light source signals LS1 to LS6 are applied to each sample of the PCR chip 10 through the collimator at the ends of a plurality of optical fiber bundles, and the first to sixth fluorescent signals are provided to the receiver 130 through a plurality of optical fiber bundles, FIG. 5 illustrates that the first to sixth light source signals LS1 to LS6 are connected to a splitter and are directly incident on each sample of the PCR chip 10 through one single-mode fiber having a relatively small size, and the first to sixth fluorescent signals FS1 to FS6 are provided to the receiver 130 through one multi-mode fiber having a relatively large size. Hereinafter, a description overlapped with FIG. 4 will be omitted to avoid redundancy.

As illustrated in FIG. 5, a single-mode optical fiber and a multi-mode optical fiber may be attached to each other. The end of the single-mode optical fiber is inclined at a predetermined angle to provide the first to sixth light source signals LS1 to LS6 to a center part of each sample of the PCR chip 10. Accordingly, the incident first to sixth light source signals LS1 to LS6 may be bent and may be applied to the center part of the sample of the PCR chip 10. The first to sixth fluorescent signals derived from each sample may be received through the multi-mode optical fiber, and may be provided to the detection array of the receiver 130 to be converted into the electrical signal.

Furthermore, referring to FIG. 5, the first to sixth light source signals LS1 to LS6 incident on the single-mode optical fiber may be incident on the samples of the PCR chip 10 at a predetermined angle. Accordingly, the probability that the light source signal is reflected from each sample and is incident on the multi-mode optical fiber may be decreased compared to the embodiment of FIG. 4. For example, the single-mode optical fiber of FIG. 5 may be a small-diameter multi-mode optical fiber, and the splitter may be a multi-mode optical fiber beam splitter.

Figure 6:
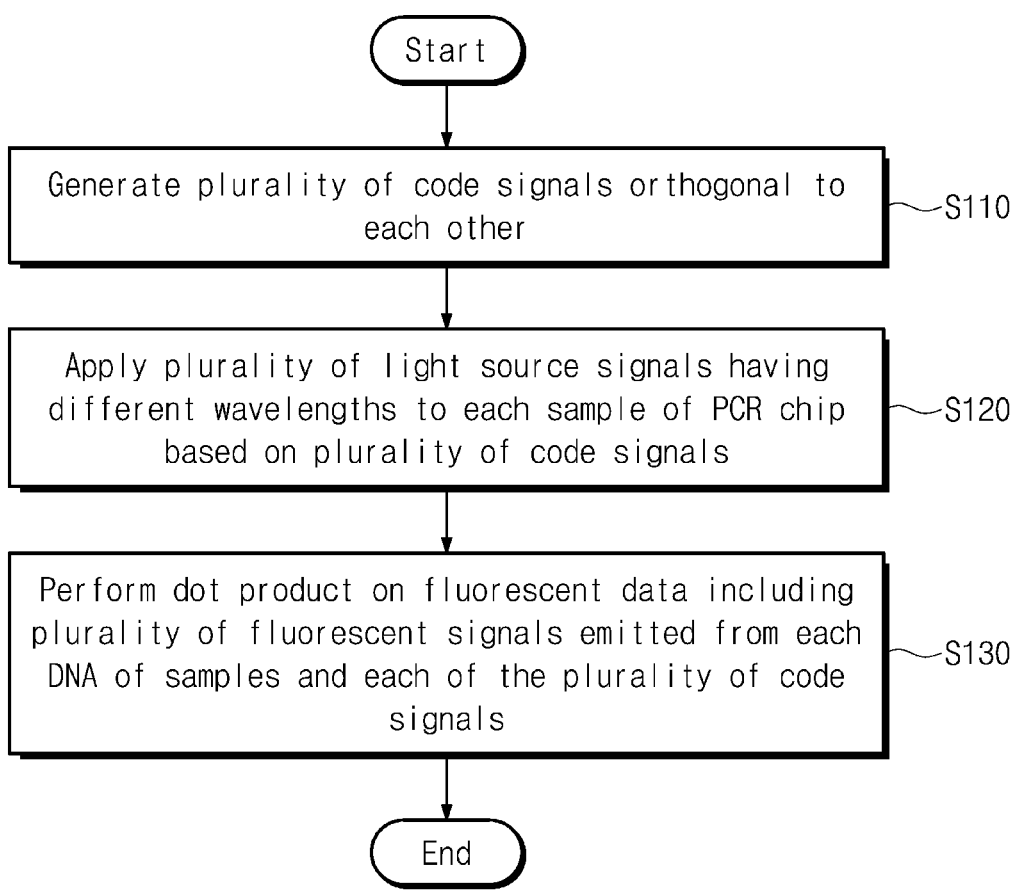
FIG. 6 is a flowchart illustrating an example of a method for a PCR diagnosis, according to an embodiment of the present disclosure.

FIG. 6 illustrates an example of a method for a PCR diagnosis, according to an embodiment of the present disclosure. Hereinafter, it will be described with reference to FIG. 1 together with FIG. 6.

In operation S110, the code generator 120 may generate the plurality of code signals CODE1 to CODEN that are orthogonal to each other. In operation S120, the code generator 120 may provide the plurality of code signals CODE1 to CODEN to the transmitter 110, and the transmitter 110 may apply the plurality of light source signals LS having different wavelengths to each sample of the PCR chip 10 based on the plurality of code signals CODE1 to CODEN. In operation S130, the receiver 130 performs the dot product on the fluorescent data FD including the plurality of fluorescent signals emitted from a phosphor attached to each DNA of the samples of the PCR chip 10, and each of the plurality of code signals CODE1 to CODEN received from the code generator 120.

According to an embodiment of the present disclosure, an issue in which a fluorescent intensity with respect to continuous light of a phosphor decreases over time may be improved. In addition, according to an embodiment of the present disclosure, since a gain increases through performing a dot product on a code signal and a fluorescent signal, even fluorescent signals having a low level may be received without noise.

The above description refers to embodiments for implementing the present disclosure. Embodiments in which a design is changed simply or which are easily changed may be included in the present disclosure as well as an embodiment described above. In addition, technologies that are easily changed and implemented by using the above embodiments may be included in the present disclosure. While the present disclosure has been described with reference to embodiments thereof, it will be apparent to those of ordinary skill in the art that various changes and modifications may be made thereto without departing from the spirit and scope of the present disclosure as set forth in the following claims.

What is claimed is:

1. A polymerase chain reaction (PCR) diagnosis apparatus comprising:
    a transmitter including a multi-wavelength light source for outputting a first light source signal and a second light source signal having different wavelengths, and configured to apply the first light source signal and the second light source signal to a PCR chip including samples each including a plurality of DNAs;
    a code generator configured to generate first code signal and second code signal corresponding to the first light source signal and the second light source signal, respectively, and being orthogonal to each other; and a receiver including a plurality of detectors with a processor configured to perform a dot product on fluorescent data and each of the first code signal and the second code signal, wherein the fluorescent data include a first fluorescent signal and a second fluorescent signal emitted from a phosphor attached to each of the plurality of DNAs, wherein the first fluorescent signal is emitted from a first phosphor attached to a first DNA among the plurality of DNAs in response to the first light source signal, and the second fluorescent signal is emitted from a second phosphor attached to a second DNA among the plurality of DNAs in response to the second light source signal.

2. The PCR diagnosis apparatus of claim 1, wherein the first code signal and the second code signal include a first section having a logic high value and a second section having a logic low value, and a time of the first section is the same as a time of the second section.

3. The PCR diagnosis apparatus of claim 2, wherein, after substituting values of the first section with '1' and values of the second section with '−1', a dot product result on the first code signal and the second code signal is '0'.

4. The PCR diagnosis apparatus of claim 2, wherein:
a level of the first fluorescent signal during the first section of the first code signal and a level of the second fluorescent signal during the first section of the second code signal are values dependent on the number of PCR cycles, and
a level of the first fluorescent signal during the second section of the first code signal and a level of the second fluorescent signal during the second section of the second code signal correspond to a level of noise.

5. The PCR diagnosis apparatus of claim 4, wherein:
the receiver includes a detection array configured to convert the fluorescent data into an electrical signal, the detection array includes the plurality of detectors configured to receive the fluorescent data,
the fluorescent data is a combined signal obtained by detecting the first fluorescent signal and the second fluorescent signal, and the number of bits of the fluorescent data is equal to the number of bits of the first code signal and the second code signal, and
each of the plurality of detectors substitutes values of the first section of the first code signal and the second code signal with '1', substitutes values of the second section of the first code signal and the second code signal with '−1', and performs a dot product on the fluorescent data and each of the first code signal and the second code signal.

6. The PCR diagnosis apparatus of claim 1, wherein the receiver includes a filter configured to remove the first light source signal and the second light source signal reflected from the samples of the PCR chip.

7. The PCR diagnosis apparatus of claim 1, wherein the first light source signal and the second light source signal are applied to the samples of the PCR chip through a central bundle among a plurality of optical fiber bundles, and the first fluorescent signal and the second fluorescent signal are provided to the receiver through outer bundles among the plurality of optical fiber bundles.

8. The PCR diagnosis apparatus of claim 1, wherein the first light source signal and the second light source signal are applied to the samples of the PCR chip through a single-mode optical fiber, and the first fluorescent signal and the second fluorescent signal are provided to the receiver through a multi-mode optical fiber.

9. The PCR diagnosis apparatus of claim 8, wherein the single-mode optical fiber is inclined at a predetermined angle such that the first light source signal and the second light source signal are applied to a center part of the samples of the PCR chip.

* * * * *